United States Patent

Uluyol et al.

(10) Patent No.: US 9,205,845 B2
(45) Date of Patent: Dec. 8, 2015

(54) SYSTEM AND METHOD FOR DETECTING SPALL INITIATION AND DEFINING END OF LIFE IN ENGINE COMPONENTS

(71) Applicant: HONEYWELL INTERNATIONAL INC., Morristown, NJ (US)

(72) Inventors: Onder Uluyol, Fridley, MN (US); Chris Hickenbottom, Phoenix, AZ (US)

(73) Assignee: Honeywell International Inc., Morris Plains, NJ (US)

(*) Notice: Subject to any disclaimer, the term of this patent is extended or adjusted under 35 U.S.C. 154(b) by 347 days.

(21) Appl. No.: 13/901,995

(22) Filed: May 24, 2013

(65) Prior Publication Data

US 2013/0332045 A1    Dec. 12, 2013

Related U.S. Application Data

(60) Provisional application No. 61/656,814, filed on Jun. 7, 2012.

(51) Int. Cl.
| | |
|---|---|
| G06F 19/00 | (2011.01) |
| B60W 50/00 | (2006.01) |
| F16N 29/00 | (2006.01) |
| G01N 33/28 | (2006.01) |

(52) U.S. Cl.
CPC ............. *B60W 50/00* (2013.01); *F16N 29/00* (2013.01); *F16N 2250/32* (2013.01); *G01N 33/2858* (2013.01)

(58) Field of Classification Search
CPC .................................................... F01D 41/222
USPC ................................ 701/101, 107, 114; 73/10
See application file for complete search history.

(56) References Cited

U.S. PATENT DOCUMENTS

| | | | |
|---|---|---|---|
| 3,981,584 | A | 9/1976 | Guymer |
| 4,103,229 | A | 7/1978 | Gear |
| 4,219,805 | A | 8/1980 | Magee et al. |

(Continued)

FOREIGN PATENT DOCUMENTS

| | | |
|---|---|---|
| EP | 2014877 A2 | 1/2009 |
| EP | 2273075 A2 | 1/2011 |
| WO | 9836251 A1 | 8/1998 |
| WO | 0004361 A1 | 1/2000 |

OTHER PUBLICATIONS

USPTO Office Action for U.S. Appl. No. 12/790,340 dated Nov. 7, 2013.

(Continued)

*Primary Examiner* — John Kwon
(74) *Attorney, Agent, or Firm* — Ingrassia Fisher & Lorenz, P.C.

(57) ABSTRACT

A system and method are provided for detecting a spall in an engine. The vehicle, for example, may include, but is not limited to an engine, an oil debris sensor coupled to the engine, a communications system, and a processor communicatively coupled to the oil debris sensor and the communications system. The processor may be configured to increment a counter when the oil debris sensor detects a particle over a predetermined size, increment the counter when a mass of a plurality of particles under the predetermined size exceeds a predetermined mass threshold, transmit, via the communications system, a first message when the counter exceeds a predetermined counter threshold, and reset the counter after predetermined amount of time.

20 Claims, 3 Drawing Sheets

(56) References Cited

U.S. PATENT DOCUMENTS

| | | | |
|---|---|---|---|
| 4,302,754 | A | 11/1981 | Magee et al. |
| 4,731,578 | A | 3/1988 | Tsaprazis |
| 5,566,092 | A | 10/1996 | Wang et al. |
| 6,049,381 | A | 4/2000 | Reintjes et al. |
| 6,525,531 | B2 | 2/2003 | Forrest et al. |
| 6,711,523 | B2 | 3/2004 | Bechhoefer et al. |
| 6,711,952 | B2 | 3/2004 | Leamy et al. |
| 7,886,875 | B2 * | 2/2011 | Shevchencko et al. ...... 184/6.11 |
| 7,895,016 | B2 | 2/2011 | Vittal et al. |
| 8,056,400 | B2 | 11/2011 | Reintjes et al. |
| 2002/0140564 | A1 * | 10/2002 | Danyluk et al. ............... 340/603 |
| 2005/0119840 | A1 | 6/2005 | Astley et al. |
| 2007/0137935 | A1 | 6/2007 | Craig |
| 2009/0014245 | A1 * | 1/2009 | Shevchenko et al. .......... 184/6.4 |
| 2009/0240471 | A1 | 9/2009 | Novis |
| 2010/0030492 | A1 | 2/2010 | Kar et al. |
| 2010/0076693 | A1 * | 3/2010 | Liang et al. ..................... 702/22 |
| 2012/0086445 | A1 * | 4/2012 | Bradley et al. ................ 324/251 |
| 2013/0000376 | A1 * | 1/2013 | Allam ............................ 73/1.02 |

OTHER PUBLICATIONS

EP search report for EP 13169791.4-1603/2672164 dated Feb. 13, 2015.

USPTO Office Action for U.S. Appl. No. 12/790,340 dated Mar. 13, 2014.

USPTO Office Action for U.S. Appl. No. 12/790,340 dated Apr. 10, 2012.

USPTO Office Action for U.S. Appl. No. 12/790,340 dated Nov. 16, 2012.

EP Search Report, for Application No. EP 10 196 610.9 dated Jul. 13, 2011.

EP Communication, for Application No. EP 10 196 610.9 dated Jul. 26, 2011.

USPTO Notice of Allowance; Notification date Jun. 8, 2015, for U.S. Appl. No. 12/790,340.

USPTO Office Action for U.S. Appl. No. 12/790,340 dated Jan. 29, 2015.

USPTO Office Action for U.S. Appl. No. 12/790,340 dated Oct. 2, 2014.

EATON Electronic Oil Debris Monitoring System; Jul. 2009; URL: http://www.eaton.com/ecm/groups/public/@pub/@eaton/@aero/documents/content/ct_194536.pdf.

Miller, J.L., et al.: In-line Oil Debris Monitor for Aircraft Engine Condition Assessment; 2000; URL: http://www.ewp.rpi.edu/hartford/~ernesto/F2006/EP/Aids/Papers/Figueroa-Rodriguez/Miller.pdf.

Howe, B., et al.; In-line Oil Debris Monitor (ODM) for Helicopter Gearbox Condition Assessment; 1998; URL: http://www.dtic.mil/dtic/tr/fulltext/u2/a347503.pdf9.

* cited by examiner

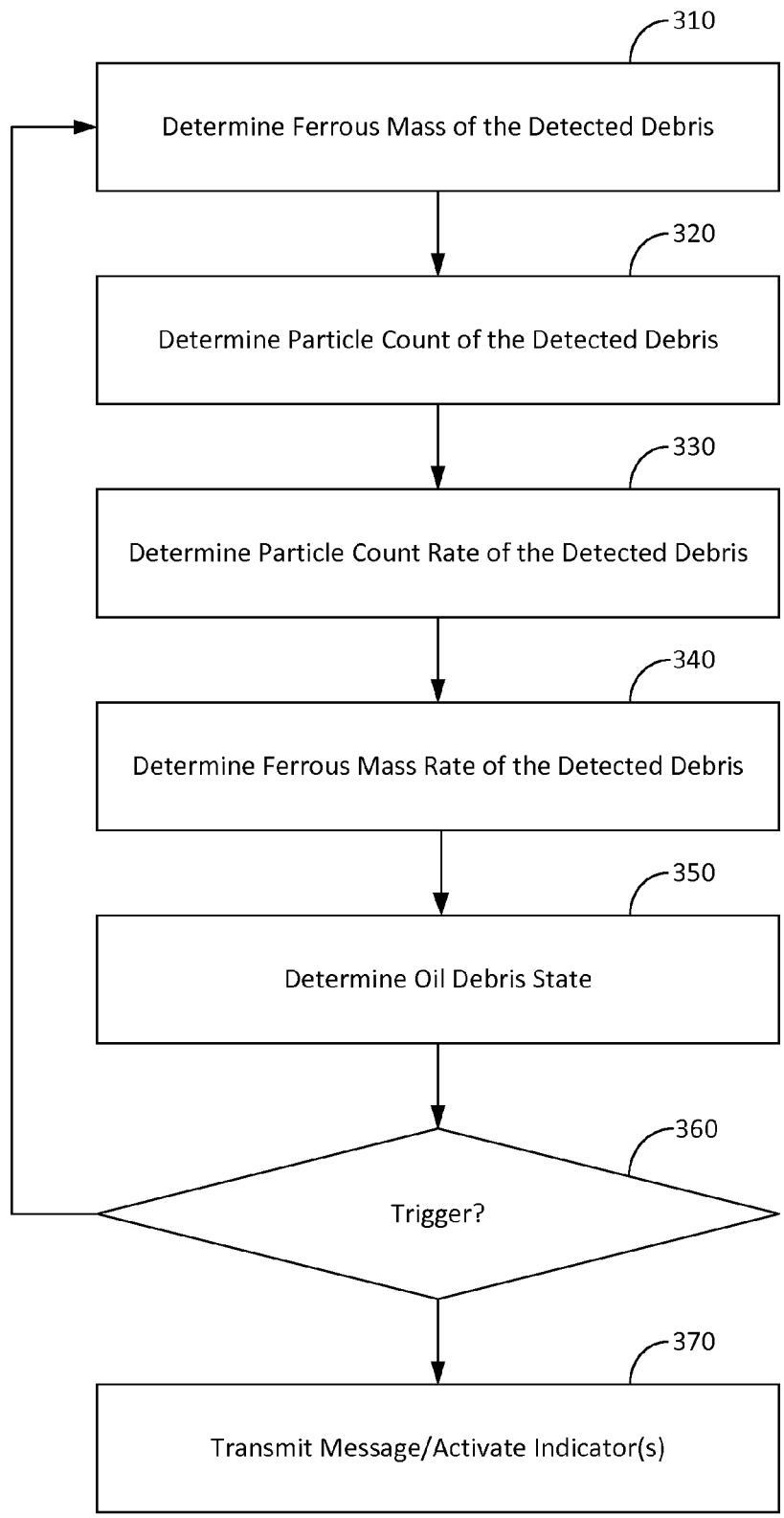

SYSTEM AND METHOD FOR DETECTING SPALL INITIATION AND DEFINING END OF LIFE IN ENGINE COMPONENTS

CROSS-REFERENCE TO RELATED APPLICATION(S)

This application claims the benefit of U.S. provisional patent application Ser. No. 61/656,814, filed Jun. 7, 2012.

TECHNICAL FIELD

The present disclosure generally relates to health monitoring, and more particularly relates to a system and method for detecting spall initiation and defining end of life.

BACKGROUND

A mechanical health monitoring system for rotating machinery has to two primary objectives. One primary objective is issuing an advance warning of an impending failure. The other primary objective is preventing mission aborts and costly repairs due to primary and secondary damage. The advance warning period mentioned in the first objective can be extended by either detecting a spall early and with high confidence or by delaying the end of life as late as possible. The current practice is based on the manual inspection of an electronic chip detector and interpretation of the debris observed via human eye. The assessment of the mechanical health is based on the count of large particles and the frequency of such particles appearing over multiple inspections. The second objective demands that the end of life estimation should be highly accurate to avoid functional failure. The technical challenge is that while the incubation phase of a spall could last several tens of hours, the steady growth and rapid growth phases of a spall last in the order of hours and minutes respectively. The current practice for determining the end of life when utilizing an oil debris sensor is based on the accumulation of debris that covers the area between the two rolling elements on an inner race. The debris mass for such damage can be estimated, assuming that the fault is an inner race spall. However, the mass estimate is known to be only a rough order estimate. Also, the transition to rapid growth typically occurs roughly when the spall spans two rolling elements, but this is not precise, and can result in the end of life indication coming too close to functional failure. An indicator based solely on the debris mass could jeopardize the mission in cases where the fault does not progress like a typical inner race spall.

Therefore what is needed is automated continuous monitoring of the mechanical health of the rotating equipment to detect a spall as early as possible to allow enough time to schedule a repair and to detect the end of life with high confidence at the onset of a steady growth phase before it transitions in the rapid growth phase.

BRIEF SUMMARY

In one embodiment, for example, a vehicle is provided. The vehicle may include, but is not limited to an engine, an oil debris sensor coupled to the engine, a communications system, and a processor communicatively coupled to the oil debris sensor and the communications system. The processor may be configured to increment a counter when the oil debris sensor detects a particle over a predetermined size, increment the counter when a mass of a plurality of particles under the predetermined size exceeds a predetermined mass threshold, transmit, via the communications system, a first message when the counter exceeds a predetermined counter threshold, and reset the counter after predetermined amount of time.

In another embodiment, A method for detecting a spall in an engine, is provided. The method may include, but is not limited to incrementing a counter when an oil debris sensor detects a particle over a predetermined size, incrementing a counter when a collective mass of a plurality of particles under the predetermined size exceeds a predetermined mass threshold, transmitting, via a communications system, a first message when the counter exceeds a predetermined counter threshold, and resetting the counter after predetermined amount of time

BRIEF DESCRIPTION OF THE DRAWINGS

The detailed description will hereinafter be described in conjunction with the following drawing figures, wherein like numerals denote like elements, and wherein:

FIG. 3 is a flow chart illustrating a method for executing an exemplary second stage analysis for detecting a spall in an oil line, in accordance with an embodiment.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
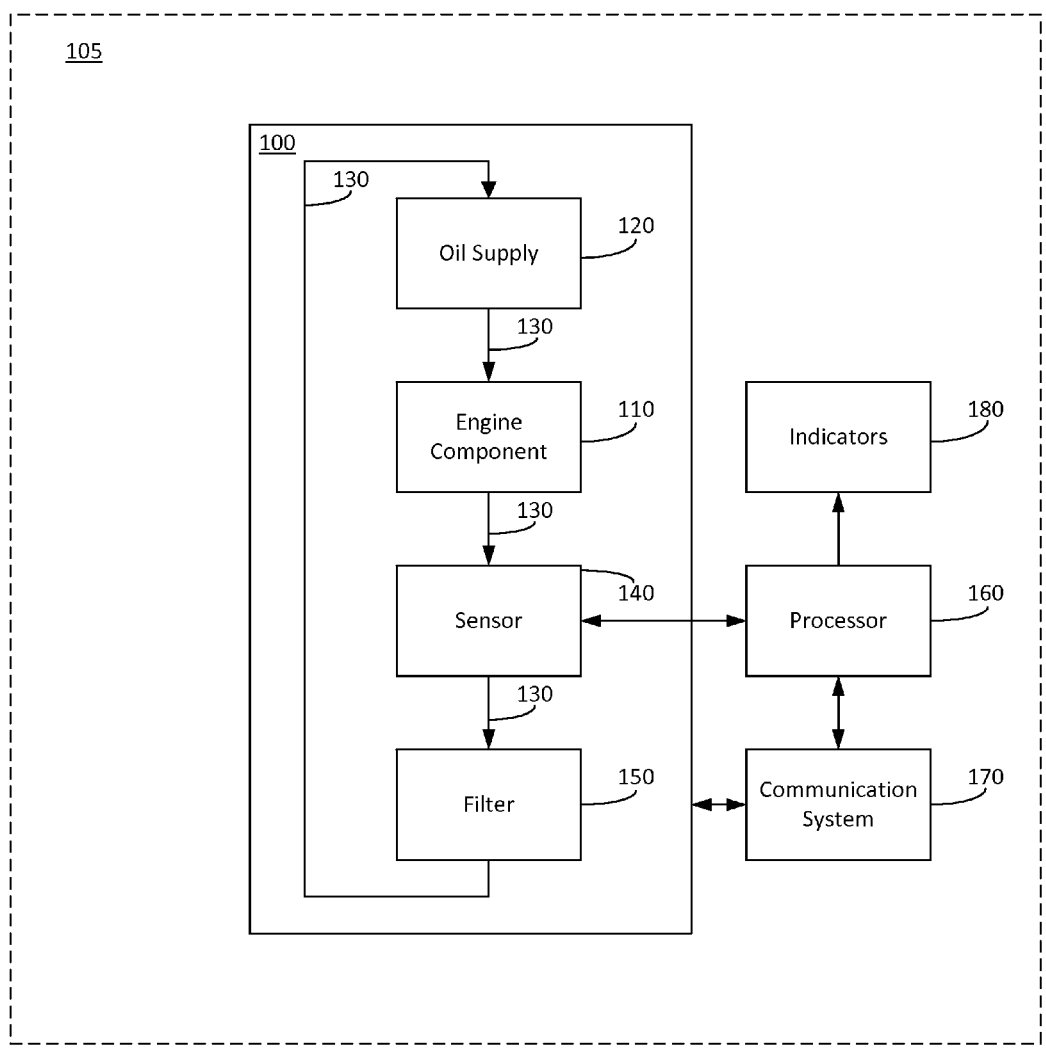
FIG. 1 is a block diagram of an engine 100, in accordance with an embodiment.

FIG. 1 is a block diagram of an engine 100, in accordance with an embodiment. The engine 100 may be an engine for a vehicle, such as an aircraft, a spacecraft, an automobile, or a marine vehicle, gearboxes, such as helicopter gearboxes, or for a power generator using wind, hydro, or thermal energy, illustrated via block 105. In one embodiment, for example, the engine 100 may be a turbine engine for an aircraft. However, one of ordinary skill in the art would recognize that the engine 100 may be any type of engine. The engine 100 includes at least one engine component 110 that utilizes oil for lubrication. In one embodiment, for example, the engine component 110 may be a bearing. In other embodiments, for example, the engine component 110 may be gears, shafts, gerotors, cams, any other oil-wetted component, or any combination thereof.

The engine 100 further includes an oil supply 120 which houses oil and feeds the oil to the at least one engine component 110 through an oil line 130. The engine 100 further includes at least one oil debris sensor 140 in line with the oil line 130 between the at least one engine component and an oil filter 150. The filter 150 captures debris in the oil line 130 before the oil returns to the oil supply 120.

In one embodiment, for example, the at least one debris sensor 140 is an oil debris monitoring (ODM) sensor. The oil debris sensor 140, hereinafter referred to as the ODM sensor 140, monitors the oil line 130 for debris. The debris may come from a variety of sources, including the engine component 110. Accordingly, the debris detected by the ODM sensor 140 may be indicative of damage to the engine component 110. The ODM sensor 140 may monitor the number of debris particles flowing through the oil line 130, the mass of the debris particles, the mass rate of the particles and the count rate of the particles. The data monitored by the ODM sensor 140 may be transmitted to a processor 160 which processes the data to determine if a spall has begun to develop, as discussed in further detail below. While the processor 160 is depicted as being external to the engine 100 in FIG. 1, the processor 160 may be internal to the engine 100, disposed anywhere within the vehicle or power system utilizing the engine 100, or the processor 160 may be located remotely. When the processor 160 is located remotely, the engine 100 or the vehicle or power system utilizing the engine 100 includes a communication system 170 to transmit the data. In one embodiment, for example, the processor 160 is communicatively coupled to a communication system 170. The communication system 170 may be a radio frequency communication system or any other type of communication system. As discussed in further detail below, the processor 160 may utilize the communication system 170 to send messages to maintenance technicians when the processor determines that a spall is or may be developing. The processor 160 may also be connected to one or more audio or visual indicators 180 on the vehicle or power system 105. The processor 160 may utilize the one or more audio or visual indicators 180 to warn a pilot or operator that maintenance or some other action (such as shutting down the engine) of the engine 100 is required immediately, as discussed in further detail below.

Figure 2:
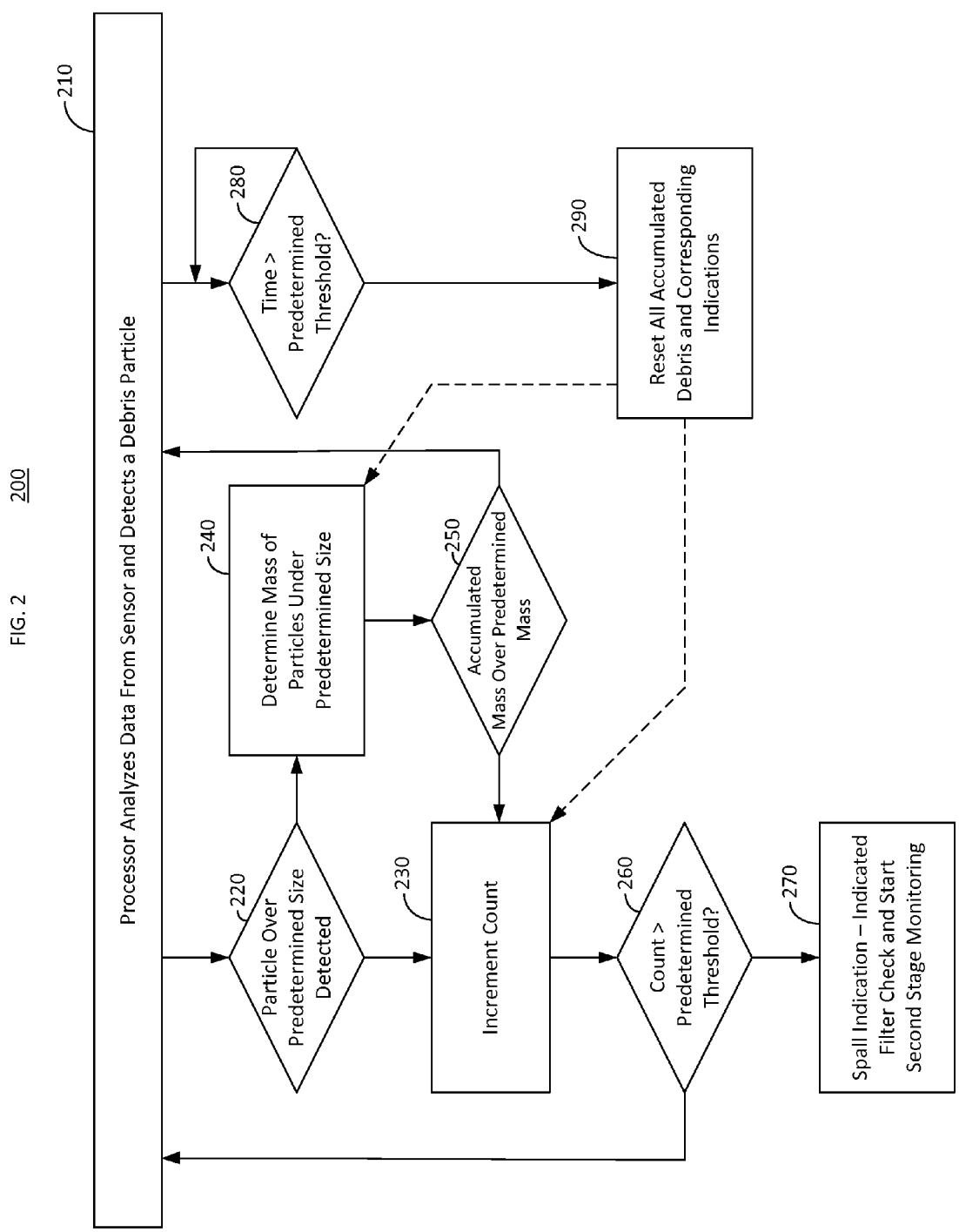
FIG. 2 is a flow chart illustrating a method for detecting a spall in an oil line, in accordance with an embodiment.

FIG. 2 is a flow chart illustrating a method 200 for detecting a spall in an oil line, such as the oil line 130 illustrated in FIG. 1. As discussed above, a sensor, such as the ODM sensor 140 illustrated in FIG. 1, sends monitoring data to a processor. The processor analyzes the data to determine when a particle is detected. (Step 210). In one embodiment, for example, the processor may analyze the data from the ODM sensor 140 to determine when a change in an electromagnetic field has occurred, indicating a debris particle. In one embodiment, for example, the processor may poll the ODM sensor 140 for data at a certain frequency and assign a timestamp to each sample. When a particle is detected, the processor determines if the detected particle is over a predetermined size. (Step 220). In one embodiment, for example, the processor may analyze the data from the ODM sensor 140 and determine the size of the debris particle based upon the change in an electromagnetic field. The predetermined size may be indicative of a medium sized debris particle. In one embodiment, for example, a medium sized particle may be 375 micron, however, the predetermined size can vary depending upon the engine and a desired sensitivity. Each time a particle over the predetermined size is detected, the processor increments a debris count. (Step 230).

If the detected particle is not over the predetermined size, the processor further analyzes the data to determine when the mass of all of the accumulated debris particles under the predetermined size is greater than a predetermined mass. (Steps 240 and 250). The processor, for example, may store a mass of each detected debris particle under the predetermined size in a buffer. In one embodiment, for example, the predetermined mass may be approximately equal to the mass of a medium sized particle, however, the predetermined mass can vary depending upon the engine and a desired sensitivity. Each time the accumulated mass is greater than the predetermined mass, the processor increments a debris count. (Step 230). The processor monitors the debris count to determine when the debris count is greater than a predetermined threshold. (Step 260). In one embodiment, for example, the predetermined threshold may be four. In other words, the processor determines if four medium or larger particles, the equivalent of four medium particles in smaller particles, or some combination thereof have passed through the oil line. In other embodiments the predetermined threshold may vary depending upon the engine and the desired sensitivity of the system. If the predetermined threshold is not exceeded, the processor continues to monitor the data received from the ODM sensor. (Step 210). If the predetermined threshold has been exceeded, a potential spall may have begun to develop in an engine component and the processor begins a second stage monitoring, as discussed in further detail below. (Step 270). In one embodiment, for example, the processor may also indicate that an oil filter check is needed. The processor, for example, may send the indication to a technician via the communication system 170. The technician, upon inspecting the oil filter 150 can analyze the debris to determine if further action is necessary based upon the debris collected by the oil filer 150.

The processor, after detecting a debris particle also starts a timer. (Step 280). If the timer exceeds a predetermined timer threshold, the processor resets the particle count from step 230 and the accumulated mass count from step 240. (Step 290). Accordingly, a potential spall indication in step 270 and the second stage analysis can only be achieved if the particle count from step 230 exceeds the predetermined particle count threshold before the predetermined timer threshold has been exceeded. In one embodiment, for example, the predetermined time threshold may be two-hundred and fifty hours. If the debris does not indicate a fault progression within the predetermined time threshold, the debris is assumed to be normal debris from normal wear and tear on the engine components.

FIG. 3 is a flow chart illustrating a method 300 for executing an exemplary second stage analysis for detecting a spall in an oil line, such as the oil line 130 illustrated in FIG. 1. As discussed in further detail below, a processor, such as the processor 160 illustrated in FIG. 1, determines a single fused value, hereinafter referred to as ODM total, representing the oil debris state of the engine based upon the number of debris particles flowing through the oil line, the mass of the debris particles, the mass rate of the particles and the count rate of the particles.

The processor first determines the contribution of the ferrous mass of the detected debris particles to the ODM total. (Step 310). In one embodiment, for example, the contribution of the ferrous mass of the detected debris particles can be calculated from Equation 1.

$$f(x_m) = \begin{cases} a \frac{x_m}{\theta_{m,1}} & \text{if } x_m < \theta_{m,1} \\ (b-a)\frac{(x_m - \theta_{m,1})}{(\theta_{m,2} - \theta_{m,1})} + a & \text{if } \theta_{m,1} \le x_m < \theta_{m,2} \\ (1-b)\frac{(x_m - \theta_{m,2})}{(\theta_{m,3} - \theta_{m,2})} + b & \text{if } \theta_{m,2} \le x_m < \theta_{m,3} \\ 1 & \text{if } x_m \ge \theta_{m,3} \end{cases} \quad \text{Equation 1}$$

Where $f(x_m)$ is the contribution of the ferrous mass of the detected debris particles to the ODM total, $x_m$ is the detected ferrous mass amount, $\theta_{m,1}$ is a first ferrous mass threshold, $\theta_{m,2}$ is a second ferrous mass threshold, $\theta_{m,3}$ is a third ferrous mass threshold, a is a first ferrous mass coefficient and b is a second ferrous mass coefficient. In one embodiment, for example, the first ferrous mass threshold $\theta_{m,1}$ may be 4 mg, the second ferrous mass threshold $\theta_{m,2}$ may be 40 mg, and the third ferrous mass threshold $\theta_{m,3}$ may be 175 mg. Each ferrous mass threshold may correspond to a damage milestone typical for an engine component. For example, the first ferrous mass threshold $\theta_{m,1}$ may correspond to the mass of debris indicative of an early development of a spall for a given engine component. The second ferrous mass threshold $\theta_{m,2}$ may correspond to an amount of debris mass that would be expected from an inner race area equivalent to 60 degrees of rotation of a rolling element. The third ferrous mass threshold $\theta_{m,3}$ may correspond to the mass of debris indicative of a failure of the engine component requiring immediate servicing of the engine. In one embodiment, for example, the first ferrous mass coefficient a may be 0.1 and the second ferrous mass coefficient b may be 0.4. The values of the ferrous mass coefficients correspond to how steep and hence how sensitive to change in the mass the indicator we want.

The processor then determines the contribution of the particle count to the ODM total. (Step 320). In one embodiment, for example, the contribution of the particle count to the ODM total may be derived from Equation 2.

$$g(x_l) = \begin{cases} kx_l & \text{if } x_l < \theta_l \\ k\theta_l & \text{if } x_l \geq \theta_l \end{cases} \quad \text{Equation 2}$$

Where $g(x_l)$ is the contribution of the particle count to the ODM total, k is a particle count constant, $x_l$ is the number of particles determined to have passed through the oil line, and $\theta_l$ is a particle count threshold. As discussed above, in one embodiment the particle count threshold $\theta_l$ may be four, however, the particle count threshold $\theta_l$ can vary depending upon the engine and a desired sensitivity of system. The particle count constant k, for example, may be 0.025. As discussed in further detail below, in one embodiment the calculation of the ODM total results in a number between zero and one. Accordingly, the particle count constant k can be chosen to scale the contribution of the particle count to the ODM total. However, as those of ordinary skill in the art would recognize, the scale of the ODM total and each of the constants discussed herein can be changed.

The processor then determines the contribution of the particle count rate to the ODM total. (Step 330). In one embodiment, for example, the contribution of the particle count rate to the ODM total may be derived from Equation 3.

$$j(x_c) = \min\left(\theta_{crx}, \sum_{i=1}^{N} m \begin{cases} 1 & \text{if } x_c(i) - x_c(i-n) \geq \theta_{cr} \\ 0 & \text{if } x_c(i) - x_c(i-n) < \theta_{cr} \end{cases}\right) \quad \text{Equation 3}$$

Where $j(x_c)$ is contribution of the particle count rate to the ODM total, $x_c$ is the cumulative particle count including particles of all sizes, $\theta_{cr}$ is a count rate threshold, $\theta_{crx}$ is a count rate cap, m is a count rate constant, n is a buffer length, and N is a total number of samples. In one embodiment, for example, the count rate cap $\theta_{crx}$ may be set to 0.2, the count rate threshold $\theta_{cr}$ is thirty particles during a fifteen minute period, and m may be 0.025, which when small particle count exceeds the threshold in the given period gives them the same weighting as a medium particle. The buffer length n, for example, sets the number of samples that considered by the processor to look for the number of small particles present to be equivalent to a medium particle. If the sampling rate is 1 per minute, for example, would be 15 for a 15 min buffer.

The processor then determines the contribution of the particle mass rate to the ODM total. (Step 340). In one embodiment, for example, the contribution of the particle mass rate to the ODM total may be derived from Equation 4.

$$h(x_r) = \sum_{i=1}^{N} l \begin{cases} \log(x_r(i) - \theta_r + 1) & \text{if } x_r(i) \geq \theta_r \\ 0 & \text{if } x_r(i) < \theta_r \end{cases} \quad \text{Equation 4}$$

Where $h(x_r)$ is the contribution of the particle mass rate to the ODM total, $x_r$ is the ferrous mass rate, $\theta_r$ is a ferrous mass rate threshold, l is a ferrous mass rate constant, and N is a total number of samples. In one embodiment, for example, the ferrous mass rate threshold $\theta_r$ may be 0.1 milligrams (mg) per minute and the ferrous mass rate constant 1 may be 0.25 which weights the mass rate contribution.

While the above description states an order for calculation the ferrous mass component, the particle count component, the particle count rate component and the ferrous mass rate component, one of ordinary skill in the art would recognize that the components may be calculated in any order. After the calculation the ferrous mass component, the particle count component, the particle count rate component and the ferrous mass rate component, the processor determines the ODM total. (Step 350). In one embodiment, for example, ODM total may be determined by adding the various components in accordance with Equation 5.

$$\text{ODM Total} = f(x_m) + g(x_l) + j(x_c) + h(x_r) \quad \text{Equation 5}$$

The processor then determines if the ODM Total has exceeded one or more triggers. (Step 360). In one embodiment, for example, a first trigger may be exceeded when the ODM total is greater than 0.5. An ODM total of 0.5 is a high confidence level indication that a spall has begun to develop and that the engine will require service. In this stage, the spall is in an incubation phase. The incubation phase can last for tens of hours. Accordingly, when the ODM total is 0.5 the one or more engine components in the engine are highly unlikely to be near failure. Accordingly, the engine can continue to be in service for a significant amount of time, potentially forty to fifty hours of service or more, giving the technician's time to schedule service for the engine between flights or overnight, reducing the downtime of the vehicle. In response to the first trigger, the processor may initiate transmission of a signal to a technician to schedule the engine for service. In one embodiment, for example, if the engine is an aircraft engine, no indication may be given to a pilot that the transmission was sent to a technician when the ODM total first exceeds 0.5.

In one embodiment, for example, a second trigger may be exceeded when the ODM total is greater than 0.9. An ODM total of 0.9 or greater is a high confidence level indication that a spall is in a steady growth phase. In a steady growth phases a spall may increase in size rapidly over the course of several hours. Accordingly, when a spall is in a steady growth phases, the engine component is near failure and that immediate service of the engine is required. In response to the second trigger, the processor may alert a pilot or crew member, if the engine is aboard an aircraft or another vehicle, that immediate action is needed, though a visual and/or audio indicator on the vehicle. However, as discussed above, the incubation phase of a spall generally lasts in the tens of hours. Accordingly, the likelihood of the second trigger being reached, requiring immediate action (i.e., turning off the engine, aborting a planned flight, emergency landings, etc.) is greatly reduced.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A vehicle, comprising:

an engine;

an oil debris sensor coupled to the engine;

a communications system; and a processor communicatively coupled to the oil debris sensor and the communications system, the processor configured to:

increment a counter when the oil debris sensor detects a particle over a predetermined size;

increment the counter when a mass of a plurality of particles under the predetermined size exceeds a predetermined mass threshold;

transmit, via the communications system, a first message when the counter exceeds a predetermined counter threshold; and reset the counter when the counter does not exceed the predetermined counter threshold within a predetermined amount of time.

2. The vehicle of claim 1, wherein the processor is further configured to:

determine, when the counter exceeds the predetermined counter threshold, an oil debris state based upon a debris particle count, a debris mass count, a debris particle count rate and a debris mass rate detected by the oil debris sensor.

3. The vehicle of claim 2, wherein the processor is further configured to determine the debris mass count according to:

$$f(x_m) = \begin{cases} a\dfrac{x_m}{\theta_{m,1}} & \text{if } x_m < \theta_{m,1} \\ (b-a)\dfrac{(x_m - \theta_{m,1})}{(\theta_{m,2} - \theta_{m,1})} + a & \text{if } \theta_{m,1} \leq x_m < \theta_{m,2} \\ (1-b)\dfrac{(x_m - \theta_{m,2})}{(\theta_{m,3} - \theta_{m,2})} + b & \text{if } \theta_{m,2} \leq x_m < \theta_{m,3} \\ 1 & \text{if } x_m \geq \theta_{m,3} \end{cases}$$

where $f(x_m)$ is the debris mass count, $x_m$ is a detected ferrous mass amount, $\theta_{m,1}$ is a first ferrous mass threshold, $\theta_{m,2}$ is a second ferrous mass threshold, $\theta_{m,3}$ is a third ferrous mass threshold, a is a first ferrous mass coefficient and b is a second ferrous mass coefficient.

4. The vehicle of claim 2, wherein the processor is further configured to determine the debris particle count according to:

$$g(x_l) = \begin{cases} kx_l & \text{if } x_l < \theta_l \\ k\theta_l & \text{if } x_l \geq \theta_l \end{cases}$$

where $g(x_l)$ is the debris particle count, k is a particle count constant, $x_l$ is a number of particles detected by the oil debris sensor, and $\theta_l$ is a particle count threshold.

5. The vehicle of claim 2, wherein the processor is further configured to determine the debris particle count rate according to:

$$j(x_c) = \min\left(\theta_{crx}, \sum_{i=1}^{N} m \begin{cases} 1 & \text{if } x_c(i) - x_c(i-n) \geq \theta_{cr} \\ 0 & \text{if } x_c(i) - x_c(i-n) < \theta_{cr} \end{cases}\right)$$

where $j(x_c)$ is the debris particle count rate, $x_c$ is a particle count, $\theta_{cr}$ is a count rate threshold, $\theta_{crx}$ is a count rate cap, m is a count rate constant, n is a buffer length, and N is a number of samples.

6. The vehicle of claim 2, wherein the processor is further configured to determine the debris mass rate according to:

$$h(x_r) = \sum_{i=1}^{N} l \begin{cases} \log(x_r(i) - \theta_r + 1) & \text{if } x_r(i) \geq \theta_r \\ 0 & \text{if } x_r(i) < \theta_r \end{cases}$$

where $h(x_r)$ is the debris mass rate, $x_r$ is a ferrous mass rate, $\theta_r$ is a ferrous mass rate threshold, l is a ferrous mass rate constant, and N is a number of samples.

7. The vehicle of claim 2, wherein the processor is further configured to transmit, via the communications system, a second message when the oil debris state indicates that a spall is in an incubation phase.

8. The vehicle of claim 7, wherein the oil debris state indicates that the spall is in the incubation phase when a sum of the debris particle count, the debris mass count, the debris particle count rate and the debris mass rate is 0.5.

9. The vehicle of claim 2, wherein the processor is further configured to transmit, via the communications system, a third message when the oil debris state indicates that a spall is in a steady growth phase.

10. The vehicle of claim 9, wherein the oil debris state indicates that the spall is in the steady growth phase when a sum of the debris particle count, the debris mass count, the debris particle count rate and the debris mass rate is 0.9.

11. A method for detecting a spall in an engine, comprising:
incrementing a counter when an oil debris sensor detects a particle over a predetermined size;
incrementing the counter when a collective mass of a plurality of particles under the predetermined size exceeds a predetermined mass threshold;
transmitting, via a communications system, a first message when the counter exceeds a predetermined counter threshold; and
resetting the counter when the counter does not exceed the predetermined counter threshold within a predetermined amount of time.

12. The method of claim 11, further comprising determining, when the counter exceeds the predetermined counter threshold, an oil debris state based upon a debris particle count, a debris mass count, a debris particle count rate and a debris mass rate detected by the oil debris sensor.

13. The method of claim 12, further comprising, determining the debris mass count according to:

$$f(x_m) = \begin{cases} a\dfrac{x_m}{\theta_{m,1}} & \text{if } x_m < \theta_{m,1} \\ (b-a)\dfrac{(x_m - \theta_{m,1})}{(\theta_{m,2} - \theta_{m,1})} + a & \text{if } \theta_{m,1} \leq x_m < \theta_{m,2} \\ (1-b)\dfrac{(x_m - \theta_{m,2})}{(\theta_{m,3} - \theta_{m,2})} + b & \text{if } \theta_{m,2} \leq x_m < \theta_{m,3} \\ 1 & \text{if } x_m \geq \theta_{m,3} \end{cases}$$

where $f(x_m)$ is the debris mass count, $x_m$ is a detected ferrous mass amount, $\theta_{m,1}$ is a first ferrous mass threshold, $\theta_{m,2}$ is a second ferrous mass threshold, $\theta_{m,3}$ is a third ferrous mass threshold, a is a first ferrous mass coefficient and b is a second ferrous mass coefficient.

14. The method of claim 12, further comprising, determining the debris particle count according to:

$$g(x_l) = \begin{cases} kx_l & \text{if } x_l < \theta_l \\ k\theta_l & \text{if } x_l \geq \theta_l \end{cases}$$

where $g(x_l)$ is the debris particle count, k is a particle count constant, $x_l$ is a number of particles detected by the oil debris sensor, and $\theta_l$ is a particle count threshold.

15. The method of claim 12, further comprising, determining the debris particle count rate according to:

$$j(x_c) = \min\left(\theta_{crx}, \sum_{i=1}^{N} m \begin{cases} 1 & \text{if } x_c(i) - x_c(i-n) \geq \theta_{cr} \\ 0 & \text{if } x_c(i) - x_c(i-n) < \theta_{cr} \end{cases}\right)$$

where $j(x_c)$ is the debris particle count rate, $x_c$ is a particle count, $\theta_{cr}$ is a count rate threshold, $\theta_{crx}$ is a count rate cap, m is a count rate constant, n is a buffer length, and N is a number of samples.

16. The method of claim 12, further comprising, determining the debris mass rate according to:

$$h(x_r) = \sum_{i=1}^{N} l \begin{cases} \log(x_r(i) - \theta_r + 1) & \text{if } x_r(i) \geq \theta_r \\ 0 & \text{if } x_r(i) < \theta_r \end{cases}$$

where $h(x_r)$ is the debris mass rate, $x_r$ is a ferrous mass rate, $\theta_r$ is a ferrous mass rate threshold, l is a ferrous mass rate constant, and N is a number of samples.

17. The method of claim 12, further comprising, transmitting, via the communications system, a second message when the oil debris state indicates that the spall is in an incubation phase.

18. The method of claim 17, wherein the oil debris state indicates that the spall is in the incubation phase when a sum of the debris particle count, the debris mass count, the debris particle count rate and the debris mass rate is 0.5.

19. The method of claim 12, further comprising, transmitting, via the communications system, a third message when the oil debris state indicates that the spall is in a steady growth phase.

20. The method of claim 19, wherein the oil debris state indicates that the spall is in the steady growth phase when a sum of the debris particle count, the debris mass count, the debris particle count rate and the debris mass rate is 0.9.

* * * * *